(12) United States Patent
Cleveland

(10) Patent No.: US 6,461,034 B1
(45) Date of Patent: Oct. 8, 2002

(54) USE OF A BUBBLE PADDLE TUMBLE STIRRER TO MIX THE CONTENTS OF A VESSEL WHILE THE CONTENTS ARE BEING REMOVED

(75) Inventor: Patrick H. Cleveland, San Diego, CA (US)

(73) Assignee: V & P Scientific, Inc., San Diego, CA (US)

( * ) Notice: Subject to any disclaimer, the term of this patent is extended or adjusted under 35 U.S.C. 154(b) by 0 days.

(21) Appl. No.: 09/993,853

(22) Filed: Nov. 14, 2001

(51) Int. Cl.$^7$ .............................. B01F 7/04; B01F 13/08
(52) U.S. Cl. .................. 366/273; 366/274; 366/325.92
(58) Field of Search ............................... 366/273, 274, 366/325.92, 329.1, 342, 343, 292, 293, 297

(56) References Cited

U.S. PATENT DOCUMENTS

| | | | | |
|---|---|---|---|---|
| 147,717 A | * | 2/1874 | Warren | |
| 297,115 A | * | 4/1884 | Deis | |
| 1,665,260 A | * | 4/1928 | Grunn | |
| 3,224,929 A | * | 12/1965 | Fair | |
| 3,595,531 A | * | 7/1971 | Williams et al. | 366/273 |
| 3,997,272 A | * | 12/1976 | George | 366/274 |
| 4,144,805 A | * | 3/1979 | Cacho | 366/329.1 |
| 4,879,917 A | * | 11/1989 | Eppelmann et al. | 366/343 |
| 5,558,839 A | * | 9/1996 | Matte et al. | 366/274 |
| 6,176,609 B1 | | 1/2001 | Cleveland et al. | |

* cited by examiner

Primary Examiner—Tony G. Soohoo
(74) Attorney, Agent, or Firm—Edward W. Callan

(57) ABSTRACT

The contents of a vessel are mixed while the contents are being removed from the vessel. A bubble-paddle tumble stirrer having at least one linear array of rounded-edge blades is disposed horizontally in the vessel for rotation about the longitudinal axis of the array. The vessel contour defines openings at nodes between the blades for enabling the mixed vessel contents to be removed from within the openings by use of pipettes inserted into the openings. The openings extend to the bottom of the vessel. The vessel contour also defines a protrusion that closely matches the edge profile of the linear array of blades for defining a narrow duct when the edges of the blades rotate adjacent the matching vessel protrusion to thereby enhance turbulence in the vessel contents as the stirrer is being rotated.

28 Claims, 6 Drawing Sheets

USE OF A BUBBLE PADDLE TUMBLE STIRRER TO MIX THE CONTENTS OF A VESSEL WHILE THE CONTENTS ARE BEING REMOVED

BACKGROUND OF THE INVENTION

The present invention generally pertains to mixing the contents of a vessel and is particularly directed to mixing the contents of a vessel while the contents of the vessel are being removed.

Suspending particulates in liquids, breaking up aggregates, aeration of gases in liquids, dissolving solids in liquids, emulsifying two liquids or mixing liquids together has usually been accomplished in large vessels, bottles and flasks by direct mechanical propeller stirring, magnetic horizontal spin stirring, orbital shakers, vortexing, rocking platforms, bubblers or vibrators. Scientists often need to add these emulsions or suspended particulates into multi-well microplates (6, 12, 24, 48, 96, 384, 864, 1536 and 10,000 wells/microplate) while the contents are still being mixed as it is important that each well in the microplate receive the same amount of emulsified or suspended particulates. This is not easily done by conventional methods. Sedimentation or separation problems arise when the mixing is stopped to collect samples of the vessel contents. Many samples are very expensive, whereby it is important to remove as much of the sample as possible from the bottom of the vessel. The mixing device also should be able to accommodate pipette systems of 8, 12, 96, 384 or 1536 pipettes simultaneously for removing the mixed contents from the bottom of the vessel while such contents are being mixed in the vessel. No known prior art device is suitable.

SUMMARY OF THE INVENTION

The present invention provides a method of mixing the contents of a vessel while said contents are being removed therefrom, comprising the steps of:

(a) using as said vessel, a vessel in which a bubble-paddle tumble stirrer having a linear array of rounded-edge blades is disposed horizontally for rotation about the longitudinal axis of the array, wherein the vessel contour at one side of the array defines openings at nodes between the blades for enabling said mixed vessel contents to be removed from within said openings by use of removal means inserted into said openings; and (b) rotating the stirrer to mix said vessel contents while said contents are being removed from the vessel.

The present invention further provides a device for use in mixing the contents of a vessel while said contents are being removed therefrom, comprising: a vessel; and a bubble-paddle tumble stirrer having a linear array of rounded-edge blades disposed horizontally in the vessel for rotation about the longitudinal axis of the array to thereby mix the contents of said vessel; wherein the vessel contour at one side of the array defines openings at nodes between the blades for enabling said mixed contents to be removed from within said openings by use of removal means inserted into said openings while the stirrer is being rotated to mix said vessel contents.

Additional features of the present invention are described with reference to the detailed description of the preferred embodiments.

DETAILED DESCRIPTION

Referring to FIGS. 1, 2, 3 and 4, one preferred embodiment of a mixing device 10 according to the present invention includes a vessel 11 and a bubble-paddle-tumble stirrer 12. The stirrer 12 includes a linear array of rounded-edge blades (bubbles) 14 that is disposed horizontally in the vessel 11 for rotation about the longitudinal axis of the array. The stirrer array has a bearing 16 at each end that is captured in a notch 18 in the end walls 20 of the vessel 11. The capture of the bearings 16 in the notches 18 maintains the alignment of the stirrer 12 within the vessel 11 and facilitates the free spinning of the stirrer 12.

The vessel contour defines a protrusion 22 that closely matches the edge profile of the linear array of blades 14 for defining a narrow duct 24 when the edges of the blades 14 rotate adjacent the matching vessel protrusion 22 to thereby enhance turbulence in the vessel contents as the stirrer 12 is being rotated. By providing such a narrow duct 24 extending over the length of the stirrer 12, greater stirring efficiency and a relatively uniform shearing action are achieved by a ducted-fan type of effect as the edges of the stirrer blades 14 pass the matching vessel protrusion 22. The direct physical interaction of the blade edges and the matching protrusion 22 of the vessel 11 with the vessel contents produces a robust mixing and movement of liquids and solids in the vessel 11 that allows uniform sampling of the vessel contents to occur while mixing is taking place. This direct physical interaction and the shear forces provided by such interaction are important in mixing oil and water to make an emulsion. This direct physical interaction cannot be duplicated by orbital shaking, vortexing, rocker platform or vibration. Furthermore the power of the tumbling action is such that it will stir even viscous material like pure honey at four degrees Fahrenheit, which cannot be stirred by conventional magnetic horizontal stirring systems.

Because the blades 14 stir vertically and because the vessel protrusion 22 closely matches the edge profile of the blades 14, there are no corners and no "dead" spots for particulates to settle in.

The present invention thus provides a very simple, robust mixing method and economical and simple mixing devices for suspending particulates in liquids, dissolving a solid in a liquid, breaking up aggregates, breaking up filamentous organisms, breaking open cells, stimulating the growth of microorganisms, mixing magnetic beads, aerating gases in liquids, dissolving solids in liquids, emulsifying two compounds and/or mixing liquids together so that the contents of one or more vessels can be uniformly removed during said mixing operation and placed in other smaller vessels such as the wells of a 24, 48, 96, 384, 864, or 1536-well microplate, and other versions of microplates or vial blocks or racks of test tubes or similar liquid containers, with a minimum dead volume of the mixed contents being left behind in the mixing vessel.

Figure 3:
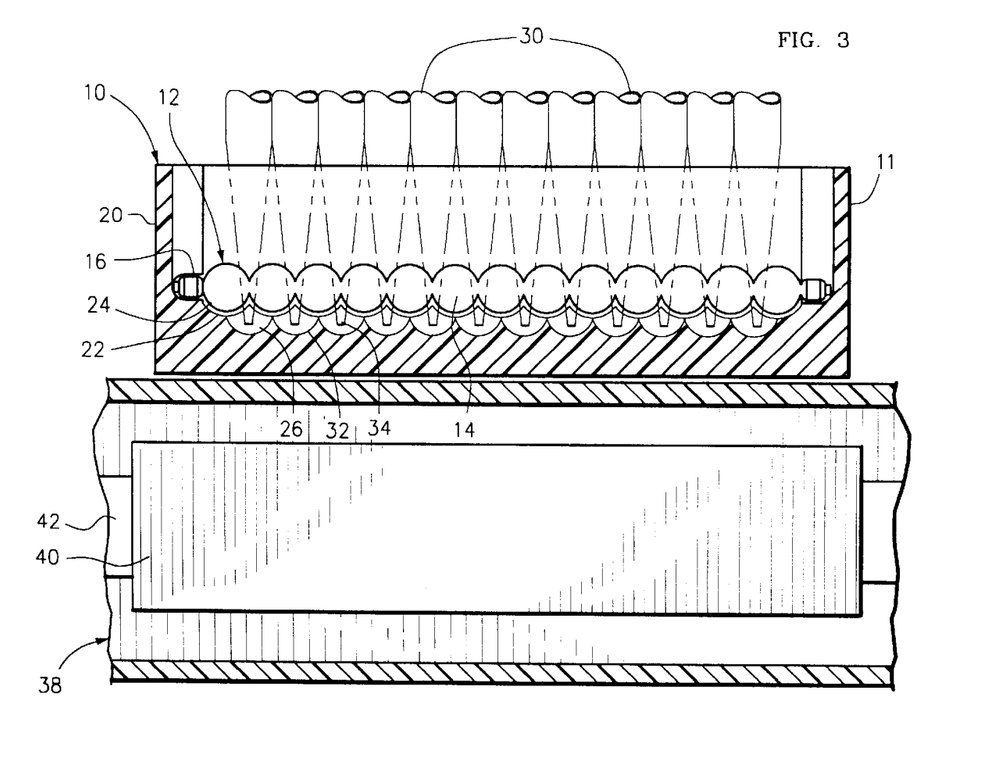
FIG. 3 is a side sectional view of the mixing device and the magnetic-drive-field assembly of FIG. 1 taken along line 3—3 in FIG. 2, with the blades rotated 90 degrees.
Figure 4:
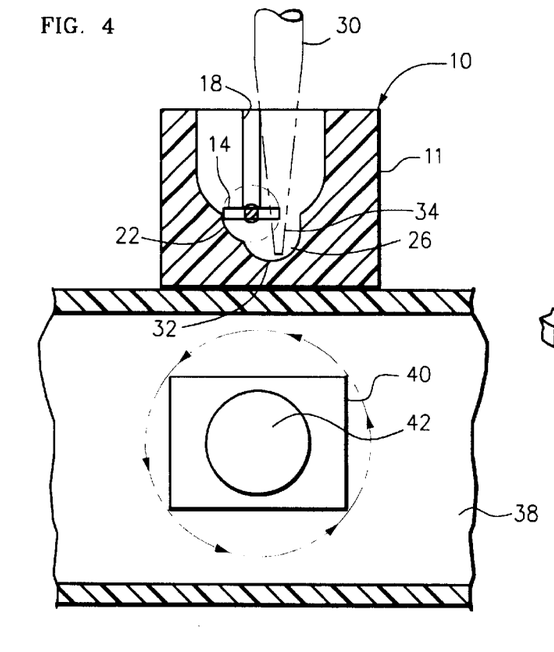
FIG. 4 is an end sectional view of the mixing device and the magnetic-drive-field assembly shown in FIG. 1.

The vessel contour defines openings 26 at nodes 28 between the blades 14 at one side of the stirrer 12 for enabling the mixed vessel contents to be removed from within the openings 26 by use of pipettes 30 inserted into the openings 26, as shown in FIGS. 3 and 4, while the stirrer 12 is being rotated to mix the vessel contents. The openings 26 extend to lowest portions of the vessel bottom 32 so that the mixed contents drain into the bottom of the openings 26. This configuration enables the mixed vessel contents adjacent the vessel bottom 32 to be removed by the pipettes 30 inserted into the openings 26. This configuration also enables removal of samples of vessel contents that have very uniform suspensions/emulsions/mixtures from each aliquot of openings 26, and with a very low dead volume of the vessel contents being left behind.

By making the individual stirrer blades 14 slightly smaller than the pitch of the pipette tips 34, the pipette tips 34 will fit near the nodes 28 between the blades 14 and will not touch the blades 14 as the stirrer 12 rotates.

Figure 5:
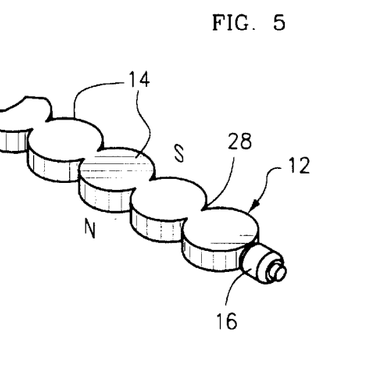
FIG. 5 is an enlarged view of a portion of the stirrer included in the mixing device shown in FIG. 1, showing the magnetic polarities of opposing edges of the stirrer blade.

The stirrer 12 can be rotated in several different ways. Referring to FIG. 5, opposing edges of the stirrer blades 14 have opposing magnetic polarities N, S for enabling the stirrer 12 to be rotated by so disposing the vessel 11 within a varying magnetic field as to cause the stirrer 12 to rotate.

Figure 1:
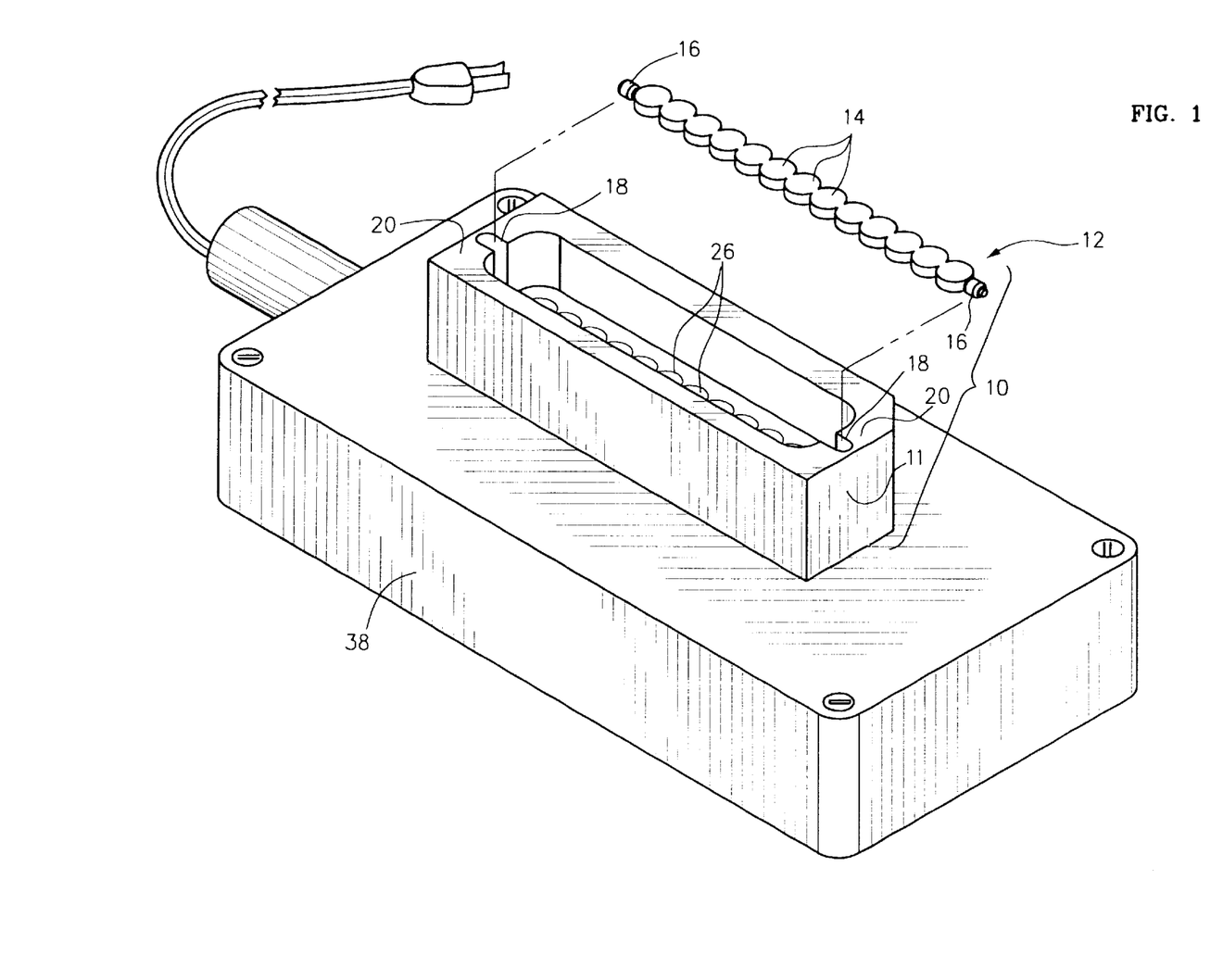
FIG. 1 is an exploded perspective view of a preferred embodiment of a mixing device according to the present invention placed on the top surface of a magnetic-drivefield assembly.
Figure 2:
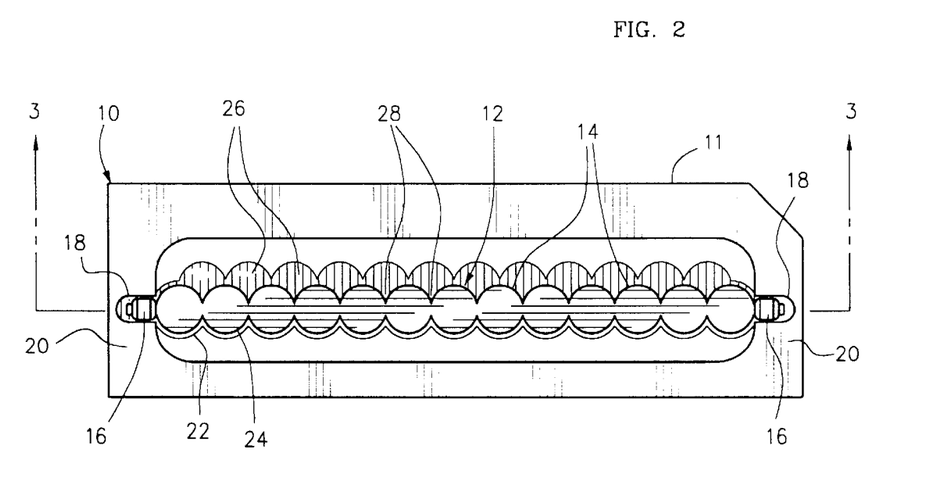
FIG. 2 is a top view of the mixing device shown in FIG. 1.
Figure 6:
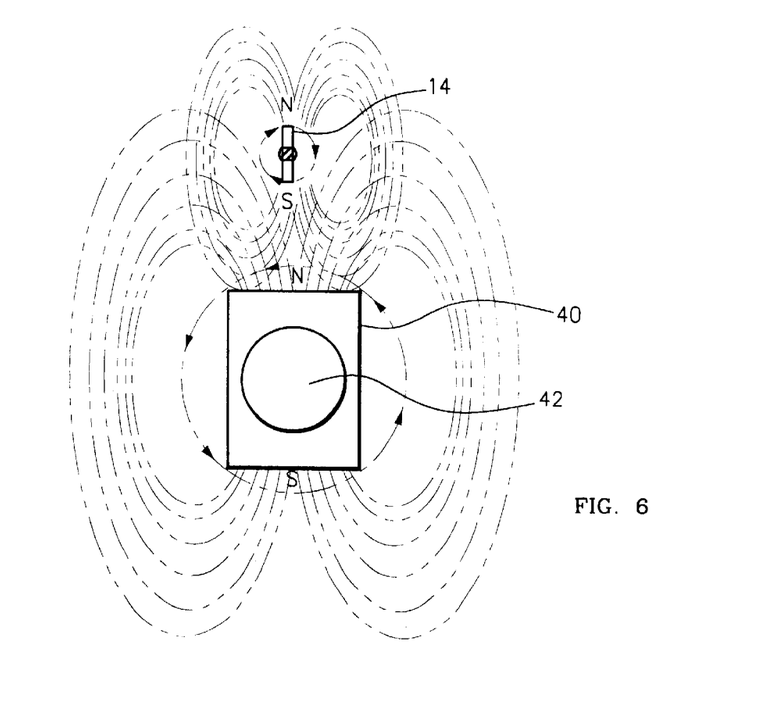
FIG. 6 illustrates the interaction between the magnetic fields of the stirrer blade and the rotary magnet shown in FIG. 4.

Referring to FIGS. 1, 3 and 4 a preferred embodiment of a magnetic-drive-field assembly 38 contains a linear rotary magnet 40 that is disposed about a shaft 42 that is horizontally disposed for rotation about its longitudinal axis. A motor (not shown) for driving the shaft 42 Iso may be included in the assembly 38. Such a magnetic-drive-field assembly 38 also may be used in the embodiments of the magnetic tumble stirring methods and devices that are described in U.S. Pat. No. 6,176,609 with reference to FIGS. 3a–3d and 8 of said patent. Opposing sides of the rotary magnet 40 have opposing magnetic polarities N, S. Preferably, the rotary magnet 40 is a permanent magnet. When the mixing device 10 is placed upon the top surface of the magneticdrive-field assembly 38 such that the longitudinal axis of the stirrer array is aligned with the longitudinal axis of the rotary magnet 40, the magnetic field of the rotary magnet 40 interacts with the magnetic field of the stirrer blades 14, as shown in FIG. 6. The magnetic poles of the stirrer blades 14 are attracted to an oppositely oriented magnetic field produced by the rotary magnet 40. This magnetic attraction causes the stirrer blades 14 to stand on a polar end and then rotate when the magnetic field of the rotary magnet 40 is rotated by rotation of the rotary magnet 40.

A speed controller (not shown) is attached to the drive shaft motor 42 to control the speed and vigor of mixing. The speed controller may be controlled by an operator or by a computer.

Several mixing devices 10 can be placed on such a magnetic-drive-field assembly 38 at any given time to enable the contents of the several different vessels to be mixed simultaneously with only a single motor.

In an alternative embodiment (not shown), the magnetic-drive-field assembly includes a linear electromagnet disposed in the same alignment as the rotary magnet 40 shown in the embodiment of FIGS. 1, 3 and 4. By periodically reversing the polarity of the electromagnet, the periodically changing interaction between the reversing magnetic field of the electromagnet and the permanent magnetic field of the stirrer blades 14 causes the stirrer 12 to rotate and thereby mix the contents of the vessel 11.

Figure 7:
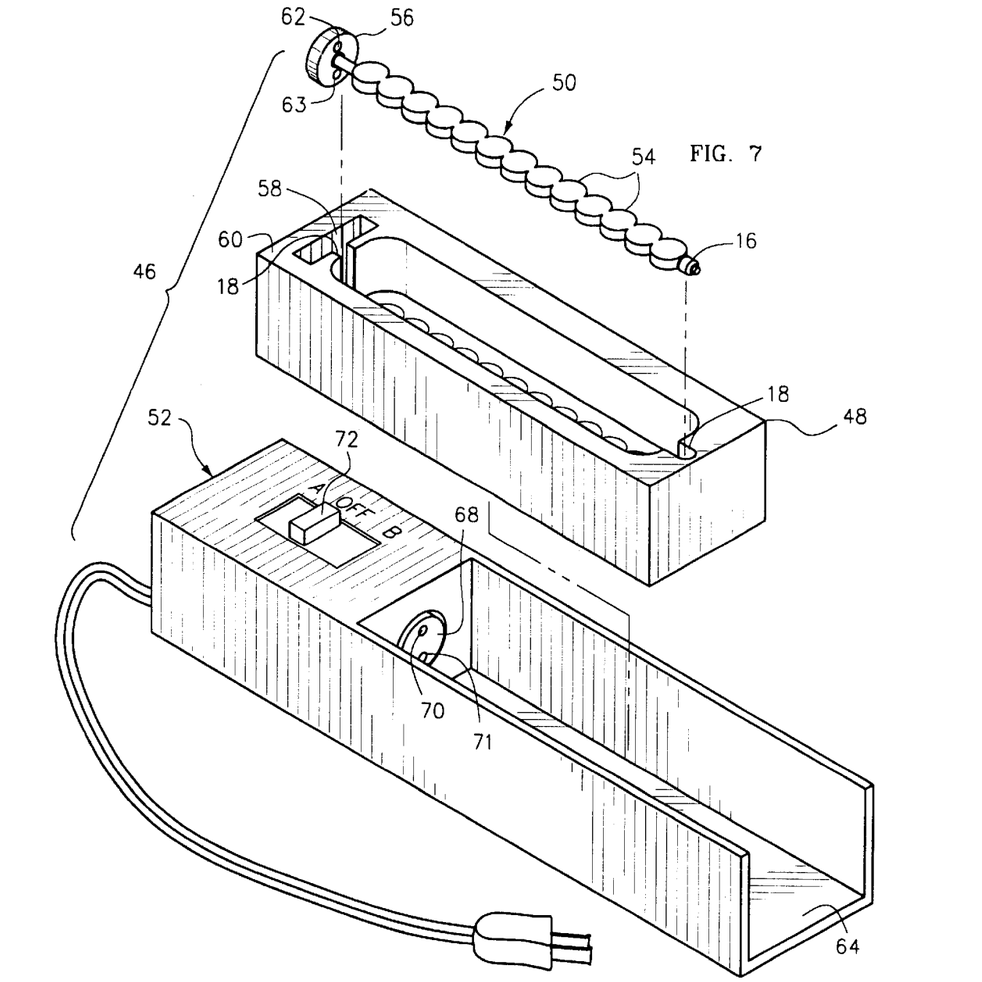
FIG. 7 is an exploded perspective view of another preferred embodiment of a mixing device according to the present invention.
Figure 8:
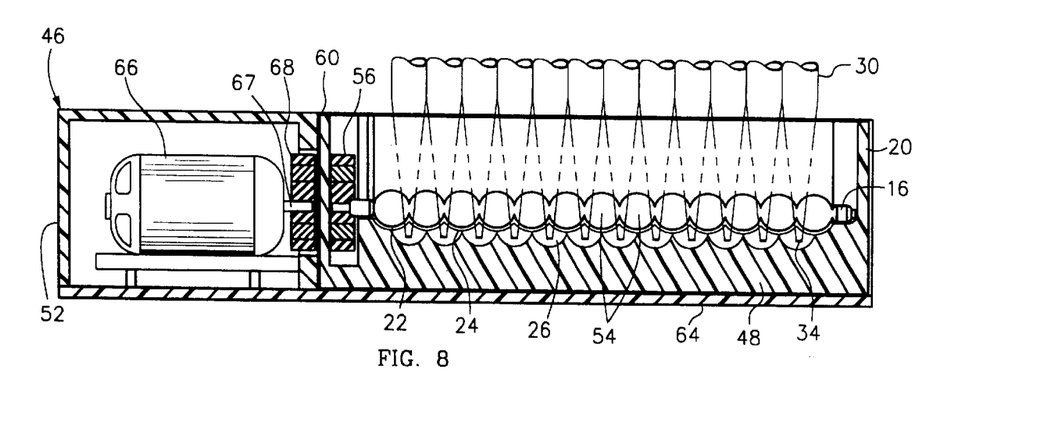
FIG. 8 is a side sectional view of the mixing device shown in FIG. 7.

The bubble-paddle-tumble stirrer can also be rotated by using a magnetic coupler attached to one end of the linear array of blades. Referring to FIGS. 7 and 8, another preferred embodiment of a mixing device 46 according to the present invention includes a vessel 48, a bubble-paddle-tumble stirrer 50 and a vessel-receiver/stirrer-drive assembly 52. The stirrer 50 is of the same construction as the stirrer 12 described above with reference to FIGS. 1–4, except that the opposing edges of the stirrer blades 54 do not have opposing magnetic polarities and a disk-shaped magnetic coupler 56 is attached to one end of the array. The stirrer 50 is disposed horizontally in the vessel 48 for rotation about the longitudinal axis of the array. The vessel 48 has the same contour as the vessel 11 described above with reference to FIGS. 1–4, except that the vessel contour further defines a chamber 58 for receiving the magnetic coupler 56. The coupler disk 54 has a bearing point in its center that rides against the outer wall 60 of the vessel 48.

The magnetic coupler 56 attached to the stirrer 50 has two small magnets 62, 63 longitudinally mounted through the thickness of the disk 56 near the disk circumference. A first magnet 62 is mounted with its north pole facing away from the stirrer 50 and a second magnet 63 is mounted 180-degrees away with its south pole facing away from the stirrer 50.

The vessel-receiver/stirrer-drive assembly 52 includes a bed 64, a rotary motor 66 having a shaft 67 and a disk-shaped magnetic coupler 68 attached to the motor shaft 67. The vessel 48 is disposed within the bed 64 of the vessel-receiver/stirrer-drive assembly 52 so that the coupler chamber 58 is disposed at the end of the bed 64 that is adjacent the magnetic coupler 68 that is attached to the motor shaft 67 to thereby magnetically couple the magnetic coupler 56 attached to the stirrer 50 to the magnetic coupler 68 that is attached to the motor shaft 67.

The magnetic coupler 68 that is attached to the motor shaft 67 is separated from the magnet coupler 56 that is attached to the stirrer 12 by the outer wall 60 of the vessel 48. The magnetic coupler 68 that is attached to the motor shaft 67 also has two small magnets 70, 71 longitudinally mounted through the thickness of the disk 68 near the disk circumference. A first magnet 70 is mounted with its south pole facing away from the motor 66 and a second magnet 71 is mounted 180-degrees away with its north pole facing away from the motor 66.

When the stirrer 50 is disposed within the vessel 48 so that the magnetic coupler 68 attached to the motor drive shaft 67 is aligned longitudinally with the magnetic coupler 56 attached to the stirrer 50, the first magnet 62 of the stirrer-array coupler 56 attracts the first magnet 70 of the motor-shaft coupler 68 and the second magnet 63 of the stirrer-array coupler 56 attracts the second magnet 71 of the motor-shaft coupler 68 to thereby magnetically couple the stirrer 50 to the motor shaft 67 for rotation. When the motor 66 is energized, the stirrer 50 is rotated to mix the contents of the vessel 48. In alternative embodiments, different configurations of magnetic coupling means may be used.

The motor 66 is connected to a variable speed controller (not shown) so that the speed of rotation of the stirrer 50 can be controlled. A switch 72 on the vessel-receiver/stirrer-drive assembly 52 is coupled to the motor 66 for enabling the motor 66 to be rotated in either of two rotary directions A or B, so that the direction of rotation of the stirrer 50 can be reversed from time to time.

In another alternative embodiment (not shown), the mixing device is constructed as described above with reference to FIGS. 1–4 except that the stirrer array is coupled to a motor shaft by a sealed bearing in an outer wall of the vessel and rotated when the motor is energized.

The embodiment of FIGS. 7 and 8 and the seal-bearing embodiment have several advantages over the above-described embodiment of FIGS. 1–5 that is powered by placement within a varying magnetic field, to wit: (a) the size of the motor necessary to rotate the stirrer is much smaller, (b) the stirrer blades don't have to be made of magnetic material, (c) it is cheaper to construct, (d) it can be used to mix suspensions of magnetic beads, whereas magnetic beads can not be mixed with magnetic means as they will be attracted to the magnet, and (e) it can stir more viscous solutions as it takes advantage of the greater strength of the magnetic coupling or a direct motor coupling through a sealed bearing.

Figure 9:
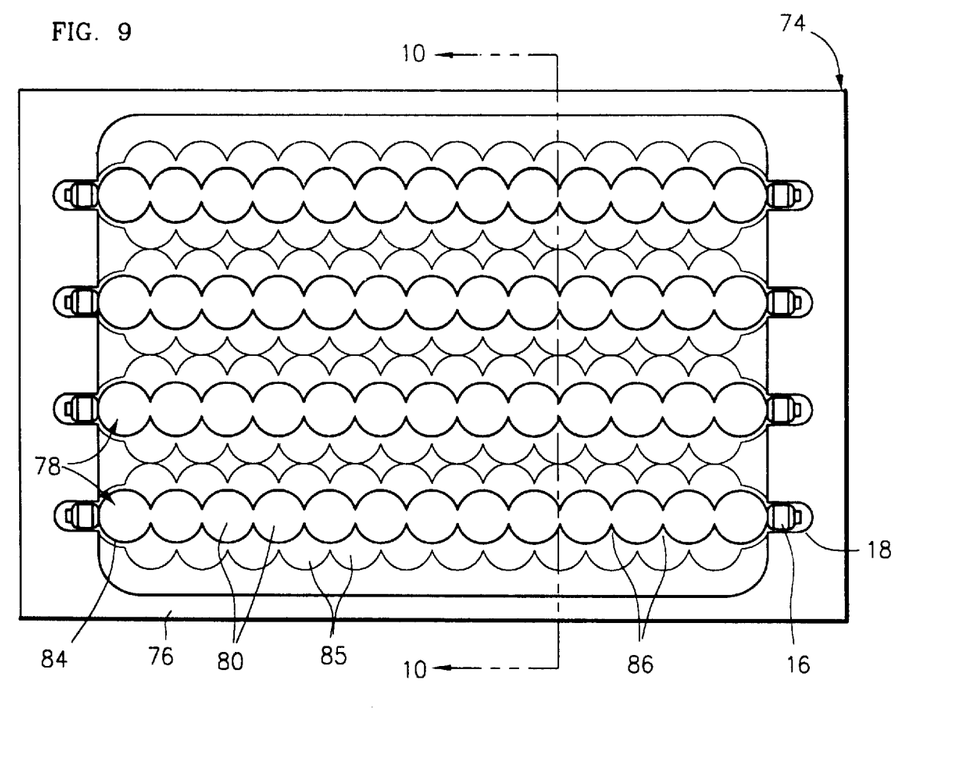
FIG. 9 is a top view of still another preferred embodiment of a mixing device according to the present invention.
Figure 10:
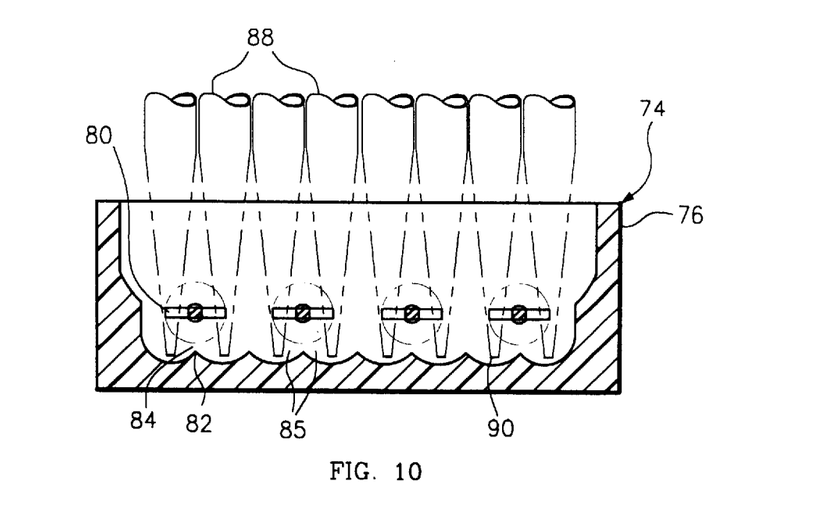
FIG. 10 is an end sectional view of the mixing device shown in FIG. 9 taken along line 10—10 in FIG. 9.

Referring to FIGS. 9 and 10, still another preferred embodiment of a mixing device 74 according to the present invention includes a vessel 76 and a plurality of bubble-paddle tumble stirrers 78 disposed in parallel within the vessel 76. Each stirrer 78 has a linear array of rounded-edge blades 80 and is disposed horizontally in the vessel 78 for rotation about the longitudinal axis of the array. Beneath each stirrer 78 the vessel contour defines a protrusion 82 that closely matches the edge profile of the respective linear array of blades 80 for defining a narrow duct 84 when the edges of the blades 80 rotate adjacent the matching vessel protrusion 82 to thereby enhance turbulence in the vessel contents as the stirrer 78 is being rotated. The vessel contour defines openings 85 at nodes 86 between the blades 80 at both of the opposing sides of each stirrer 78 for enabling the mixed vessel contents to be removed from within the openings 85 by use of pipettes 88 inserted into the openings 85. The openings 85 extend to the vessel bottom 90 for enabling the mixed vessel contents adjacent the vessel bottom 90 to be removed by the pipettes 88 inserted into the openings 85. The embodiment illustrated in FIGS. 9 and 10 includes four thirteen-blade stirrers 78 and twelve openings 85 on each side of each stirrer 78, whereby ninety-six samples of mixed vessel contents can be removed from the vessel simultaneously by use of pipettes 88 inserted into the openings 85 while the vessel contents are being mixed.

In other alternative embodiments (not shown) the mixing device includes a different number of bubble-paddle tumble stirrers of the type shown in FIGS. 9 and 10 disposed in parallel within the vessel and/or the individual stirrer arrays include a different number of blades.

The bubble paddle stirrers 12, 50, 78 are made of made stainless steel and are of different dimensions and shapes so that they will fit into a variety of vessels in combination with different systems of pipette heads (4, 6, 8, 12, 96, 384 and 1536 heads) to provide a vigorous tumble stirring action when the stirrers are rotated.

Figure 11:
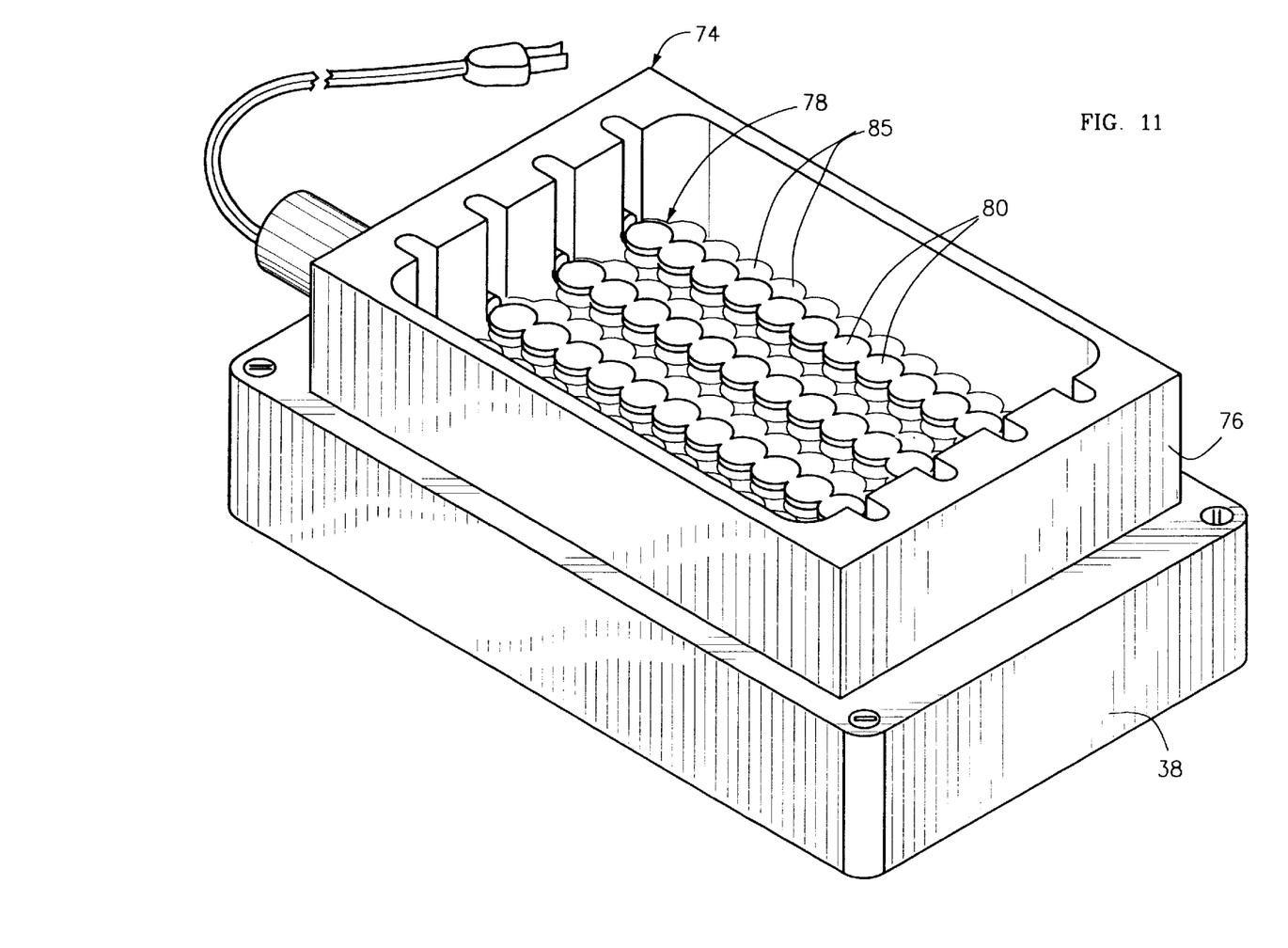
FIG. 11 is a perspective view of the mixing device shown in FIG. 9 placed on the top surface of a magnetic-drive-field assembly.

Referring to FIG. 11, the mixing device 74 of FIGS. 9 and 10 is placed upon the top surface of a magnetic-drive-field assembly, such as the magnetic-drive-field assembly 38 described above with reference to FIGS. 1, 3 and 4, in order to simultaneously rotate all four of the stirrers 78. In an alternative embodiment (not shown), the mixing device 74 is placed on the top surface of a magnetic-drive-field assembly that contains a parallel array of rotary magnets respectively attached to a plurality of shafts for rotation about their horizontal axes, such as shown in FIG. 8 of said U.S. Pat. No. 6,176,609.

The mixing devices 10, 46, 74 can be made small enough to fit on the deck of robotic work stations to thereby facilitate removal of the vessel contents. The mixing devices also can be made as large or as small as necessary to fit the application at hand.

The advantages specifically stated herein do not necessarily apply to every conceivable embodiment of the present invention. Further, such stated advantages of the present invention are only examples and should not be construed as the only advantages of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

REFERENCE NUMERALS IN DRAWING

10 mixing device
11 vessel
12 stirrer
14 blades
16 bearing
18 notch
20 vessel wall
22 protrusion
24 duct
26 opening
28 node
30 pipettes
32 vessel bottom
34 pipette tip
38 magnetic-drive-field assembly
40 rotary magnet
42 motor shaft
46 mixing device
48 vessel
50 stirrer
52 vessel-receiver/stirrer-drive assembly
54 blades
56 magnetic coupler
58 chamber
60 vessel wall
62 magnet
63 magnet
64 bed
66 motor
67 motor shaft
68 magnetic coupler
70 magnet
71 magnet
72 switch
74 mixing device
76 vessel
78 stirrer
80 blades
82 protrusion
84 duct
85 opening 86 nodes
88 pipettes
90 vessel bottom

What is claimed is:

1. A method of mixing the contents of a vessel while said contents are being removed therefrom, comprising the steps of:

(a) using as said vessel, a vessel in which a bubble-paddle tumble stirrer having a linear array of rounded-edge blades is disposed horizontally for rotation about the longitudinal axis of the array, wherein the vessel contour at one side of the array defines openings at nodes between the blades for enabling said mixed vessel contents to be removed from within said openings by use of removal means inserted into said openings; and (b) rotating the stirrer to mix said vessel contents while said contents are being removed from the vessel.

2. A method according to claim 1, wherein the vessel contour defines a protrusion that closely matches the edge profile of the linear array of blades for defining a narrow duct when the edges of the blades rotate adjacent the matching vessel protrusion to thereby enhance turbulence in the vessel contents as the stirrer is being rotated.

3. A method according to claim 2, wherein said openings extend to the vessel bottom for enabling said mixed vessel contents adjacent the vessel bottom to be removed by use of said removal means inserted into said openings.

4. A method according to claim 1, wherein said openings extend to the vessel bottom for enabling said mixed vessel contents adjacent the vessel bottom to be removed by use of said removal means inserted into said openings.

5. A method according to claim 1, wherein a plurality of said bubble-paddle tumble stirrers are so disposed in parallel within said vessel.

6. A method according to claim 5, wherein beneath each stirrer the vessel contour defines a protrusion that closely matches the edge profile of the respective linear array of blades for defining a narrow duct when the edges of the blades rotate adjacent the matching vessel protrusion to thereby enhance turbulence in the vessel contents as the stirrer is being rotated.

7. A method according to claim 6, wherein said openings extend to the vessel bottom for enabling said mixed vessel contents adjacent the vessel bottom to be removed by use of said removal means inserted into said openings.

8. A method according to claim 7, wherein the vessel contour defines said openings at both of the opposing sides of each stirrer.

9. A method according to claim 5, wherein the vessel contour defines said openings at both of the opposing sides of each stirrer.

10. A method according to claim 1, wherein opposing edges of the blades have opposing magnetic polarities, and wherein step (b) comprises the step of:

(c) so disposing the vessel within a varying magnetic field as to cause the stirrer to rotate.

11. A method according to claim 10, wherein step (c) comprises the step of:

(d) so disposing the vessel within a rotating magnetic field of a rotary magnet.

12. A method according to claim 1, wherein step (b) comprises the step of:

(c) using a magnetic coupling disposed at an end of the array to rotate the stirrer.

13. A method according to claim 1, wherein step (b) comprises the step of:

(c) from time to time, reversing the direction of said rotation.

14. A device for use in mixing the contents of a vessel while said contents are being removed therefrom, comprising:

a vessel; and a bubble-paddle tumble stirrer having a linear array of rounded-edge blades disposed horizontally in the vessel for rotation about the longitudinal axis of the array to thereby mix the contents of said vessel;

wherein the vessel contour at one side of the array defines openings at nodes between the blades for enabling said mixed contents to be removed from within said openings by use of removal means inserted into said openings while the stirrer is being rotated to mix said vessel contents.

15. A device according to claim 14, wherein the vessel contour defines a protrusion that closely matches the edge profile of the linear array of blades for defining a narrow duct when the edges of the blades rotate adjacent the matching vessel protrusion to thereby enhance turbulence in the vessel contents as the stirrer is being rotated.

16. A device according to claim 15, wherein said openings extend to the vessel bottom for enabling said mixed vessel contents adjacent the vessel bottom to be removed by use of said removal means inserted into said openings.

17. A device according to claim 14, wherein said openings extend to the vessel bottom for enabling said mixed vessel contents adjacent the vessel bottom to be removed by use of said removal means inserted into said openings.

18. A device according to claim 14, wherein a plurality of said bubble-paddle tumble stirrers are so disposed in parallel within said vessel.

19. A device according to claim 18, wherein beneath each stirrer the vessel has a contour that closely matches the contour of the respective linear array of blades for defining a narrow space in which the vessel contents are mixed as the stirrers are rotated.

20. A device according to claim 19, wherein the vessel has said opening-defining contours at both of the opposing sides of each stirrer.

21. A device according to claim 20, wherein beneath each stirrer the vessel contour defines a protrusion that closely matches the edge profile of the respective linear array of blades for defining a narrow duct when the edges of the blades rotate adjacent the matching vessel protrusion to thereby enhance turbulence in the vessel contents as the stirrer is being rotated.

22. A device according to claim 21, wherein said openings extend to the vessel bottom for enabling said mixed vessel contents adjacent the vessel bottom to be removed by use of said removal means inserted into said openings.

23. A device according to claim 22, wherein the vessel contour defines said openings at both of the opposing sides of each stirrer.

24. A device according to claim 20, wherein the vessel contour defines said openings at both of the opposing sides of each stirrer.

25. A device according to claim 14, wherein opposing edges of the blades have opposing magnetic polarities for enabling the stirrer to be rotated by so disposing the vessel within a varying magnetic field as to cause the stirrer to rotate.

26. A device according to claim 14, wherein a magnetic coupler is disposed at an end of the array to enable rotation of the stirrer by use of magnetic coupling.

27. A device according to claim 14, further comprising:

means for rotating the stirrer to thereby mix said vessel contents.

28. A device according to claim 14, further comprising:

means for from time to time reversing the direction of said rotation.

* * * * *